United States Patent
Failli

Patent Number: 5,869,524
Date of Patent: Feb. 9, 1999

[54] INDENE INHIBITORS OF COX-2

[75] Inventor: Amedeo A. Failli, Princeton Junction, N.J.

[73] Assignee: American Home Products Corporation, Madison, N.J.

[21] Appl. No.: 959,743

[22] Filed: Oct. 28, 1997

Related U.S. Application Data

[60] Provisional application No. 60/030,863 Nov. 12, 1996.

[51] Int. Cl.⁶ .................. A61K 31/34; C07D 307/33
[52] U.S. Cl. ................................ 514/473; 549/318
[58] Field of Search .................... 549/318; 514/473

[56] References Cited

U.S. PATENT DOCUMENTS

| | | |
|---|---|---|
| 3,647,858 | 3/1972 | Hinkley et al. . |
| 3,654,349 | 4/1972 | Shen et al. . |
| 5,420,153 | 5/1995 | Schiehser et al. . |

FOREIGN PATENT DOCUMENTS 0675103  10/1995  European Pat. Off. .

OTHER PUBLICATIONS

Shuman, R.F. et al., A Sterically Efficient Synthesis of (Z)–5–Fluoro–2–methyl–1–(p–methylthiobenzylidene)–3–indenylacetic Acid and Its S–Oxide, Sulindac, J. Org. Chem., 42(11), (1977) pp. 1914–1919.
Hoffsommer, R. D. et al., Structure of the Indenylacetic Acids, J. Org. Chem., 34(12), (1969) pp. 4182–4184.
Normura, K. et al., An Efficient Method for 3(C)–Acylation of Tetronic Acids, Chem. Pharm. Bull., 34(12), (1986) pp. 5188–5190.
Tanaka, K. et al., Structure–Activity Relationships in Tetronic Acids and Their Copper(II) Complexes, Chem. Pharm. Bull., 27(8), (1979) pp. 1901–1906.
Shen, T. Y. et al., Indene derivatives useful as PAF–antagonists, Chemical Abstracts, 104:5652q, (1986) pp. 513–514.
Shen, T. Y. et al., Antiinflammatory aliphatic 1–alkylidene–3–indenyl amines, Chemical Abstracts, 75:63491e, (1971) p. 428.
Brewster, K. et al., Structure of the Indene–3–acetic Acids, J Chem Soc, (1972) pp. 941–943.
Shen, T. Y. et al., Synthetic Chemistry of Sulindac and Indene Derivatives, Adv in Drug Res, Simmonds, A. B. ed., 12:4.2, (1977) pp. 149–164, 204.
Shen, T.Y., Indomethacin, Sulindac, and Their Analogues, Anti–Inflammatory and Anti–Rheumatic Drugs, CRC Press, Inc., 1985, pp. 150–159.

Primary Examiner—Patricia L. Morris
Attorney, Agent, or Firm—Arnold S. Milowsky

[57] ABSTRACT

This invention provides compounds of formula 1 having the structure

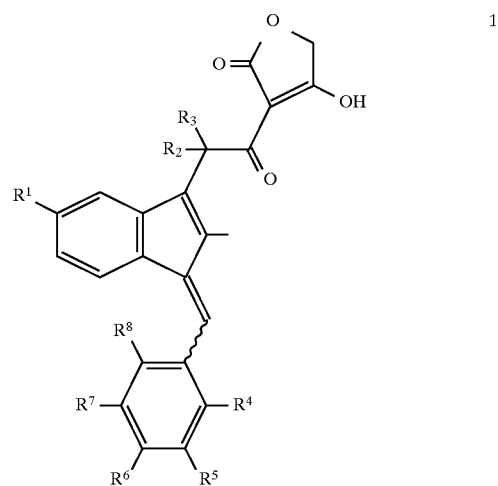

wherein:
$R^1$ is hydrogen, halogen, alkyl, alkoxy, fluoroalkoxy, trifluoromethyl, alkylthio, or $SCF_3$
$R^2$ and $R^3$ are each independently, hydrogen or alkyl, or $R^2$ and $R^3$ may be taken together to form a saturated cycloalkyl ring; and
$R^4$, $R^5$, $R^6$, $R^7$ and $R^8$ are each independently, hydrogen, alkyl, alkoxy, alkylthio, alkylsulfinyl, alkylsulfonyl, halogen, fluoroalkoxy, $CF_3$, or $SCF_3$ which are useful in the treatment of arthritic disorders, colorectal cancer, and Alzheimer's disease.

5 Claims, No Drawings

INDENE INHIBITORS OF COX-2

FIELD OF THE INVENTION

This application claims the benefit of U.S. Provisional Application No. 60/030,863, filed Nov. 12, 1996.

This invention is in the fields of antiinflammatory and anticancer pharmaceutical agents and specifically relates to compounds, compositions and methods for treating inflammation and inflammation-associated disorders, such as arthritis and Alzheimer disease, and for the treatment and/or prevention of cycloxygenase-mediated disorders such as may occur in diabetic retinopathy and tumor angiogenesis. More particularly, they may prove useful in certain types of cancer growth, such as colorectal cancer and in the treatment of Alzheimer disease.

BACKGROUND OF THE INVENTION

Prostaglandins have been known for some time to play a major role in the inflammation process, and have been shown to be involved in the pathophysiology of several chronic human diseases. They are involved as mediators of pain, edema and vascular permeability in arthritic diseases such as rheumatoid arthritis and osteoarthritis (Lewis and Kreft, *Immunopharmacol. Immunotoxicol.* 17, 607–663 (1995)). In addition, prostaglandins have been postulated to be involved in the pathophysiology of colorectal cancer (Marcus, *New Eng. J. Med.,* 333, 656–657 (1995); Huang and Heimbrook, *Exp.Opin. Invest. Drugs.,* 4 (3), 243–249 (1995)). Thus an agent that inhibits prostaglandin synthesis may be useful in treating these disorders.

The biosynthesis of prostaglandins was previously thought to be due to the action of a single cyclooxygenase enzyme on arachidonic acid to afford prostaglandin $H_2$ (Vane et al, *Postgrad. Med. J.,* 66 (Suppl 4), S2–S17 (1990); Lewis and Kreft, *Immunopharmacol. Immunotoxicol.* 17, 607–663 (1995)). This intermediate is subsequently transformed into the various members of the prostaglandin family by more distal enzymes. The clinical utility of cyclooxygenase inhibitors (often called NSAIDs; nonsteroidal antiinflammatory drugs) is well established in arthritic disorders (Brooks et al, *New Eng. J. Med.,* 324, 1716–1725 (1991)). However, these compounds also affect other prostaglandin-regulated processes not associated with inflammation but rather, with maintenance of gastrointestinal integrity and renal blood flow (Dajani et al. *J. Physiol. Pharmacol.,* 46, 3–16 (1995); Somasundaram et al. *Scand. J. Gastroenterol.,* 30, 289–299 (1995)), via a mechanism involving inhibition of prostaglandin G/H synthase or cycloxygenase (COX). Thus, at high doses often necessary to show therapeutic efficacy, most NSAIDs show severe gastric and renal side effects, including life threatening ulcers that limit their therapeutic utility. An alternative to NSAIDs is the use of corticosteroids, which have even more severe liabilities, especially when long term therapy is involved.

Under the old paradigm of a single cyclooxygenase enzyme, it appeared that the selective inhibition of prostaglandin synthesis in inflamed tissue versus inhibition of prostaglandin synthesis in G.I. tissue was unlikely unless tissue specificity could be achieved.

Recently, the discovery that there are two distinct cyclooxygenase isozymes in the arachidonic acid/prostaglandin pathway, has given rise to a new paradigm which may lead to compounds that have a separation of inhibition of prostaglandin synthesis in inflamed tissue from inhibition of prostaglandin synthesis in G.I. tissue (Haylar, *Lancet,* 346, 521–522 (1995), Lewis and Kreft, *Immunopharmacol. Immunotoxicol.* 17, 607–663 (1995)). In the new paradigm the constitutive cyclooxygenase enzyme responsible for prostaglandin synthesis in G.I. tissue is termed COX-1 and the inducible cyclooxygenase enzyme (reported by Hla and Nielson, *Proc. Ntl. Acad. Sci. USA,* 89, 7384 (1992)) responsible for prostaglandin synthesis in inflamed tissue is termed COX-2. COX-1 appears to have a physiological role being involved in maintenance of gastrointestinal integrity and renal blood flow, while COX-2 appears to be mainly responsible for the pathological effects of prostaglandins.

Several groups have reported that NSAIDS vary in their ability to inhibit COX-1 and COX-2 so that selective inhibition may be possible (O'Neill et al, *Molec. Pharmacol.,* 45, 245–254 (1994); Laneuville et al, *J. Pharmacol. Exp. Ther.,* 271, 927–934 (1994); Mitchell et al, *Proc Natl. Acad Sci. USA,* 90, 11693–11697 (1993)). The current opinion suggests that a selective inhibitor of COX-2 will have clinical efficacy in inflammatory diseases with reduced potential for gastrointestinal toxicity and renal side effects. There is evidence from animal models to support this hypothesis (Chan et. al *J. Pharmacol. Exp. Ther.* 274, 1531–1537 (1995); Masferrer et. al. *Proc. Natl. Acad. Sci. USA,* 91, 3228–3232 (1994); Seibert et al.. *Proc. Natl. Acad. Sci. USA,* 91, 12013–12017 (1994)). Moreover, this may be the mechanism behind the improved G.I. safety of the NSAID etodolac, which has been reported to show a tenfold selectivity for inhibition of COX-2 (Glaser et al. *Eur. J. Pharmacol.* 281, 107–111 (1995)).

Indomethacin, a relatively non-selective inhibitor of COX-1 and COX-2 has been shown to be useful in the treatment of Alzheimer's disease (Rogers et al., *Neurology* 43, 1609–1611 (1993)). These findings suggest that novel COX-2 inhibitors would be attractive targets for the treatment of Alzheimer disease and for antiarthritic therapy with reduced potential for gastrointestinal toxicity and renal side effects. In addition, the COX-2 enzyme has been shown to be upregulated in colorectal cancer and a selective COX-2 inhibitor may also be of use in this disease (Sano et. al. *Cancer Res..,* 55, 3785–3789 (1995); Huang and Heimbrook, *Exp. Opin. Invest. Drugs* 4 (3), 243–249, (1995)).

Certain tetronic, thiotetronic and tetramic acid derivatives are described in U.S. Pat. No. 5,420,153 as phospholipase $A_2$ inhibitors with antiinflammatory properties, and modulators of PAF-mediated biological processes useful as antifertility agents.

Certain substituted indenyl acetic acids are described in U.S. Pat. Nos. 3,654,349 and 3,647,858 with antiinflammatory, antipyretic and analgesic properties.

The above-cited patents disclose compounds that are structurally different from the compounds of the present invention. In addition, the compounds of the present invention are cycloxygenase inhibitors, and unexpectedly exhibit marked selectivity for the inhibition of COX-2 over COX-1. The compounds disclosed in each of the patents cited above unlike the compounds of the present invention, do not act as preferential inhibitors of COX-2; thus, they are not expected to exhibit any of the advantages of the compounds of the present invention, i.e. they are not expected to produce a reduced amount of side effects.

DESCRIPTION OF THE INVENTION

In accordance with this invention, there are provided COX-2 inhibitors which are useful as antiarthritic, anticancer and anti-Alzheimers agents of formula I:

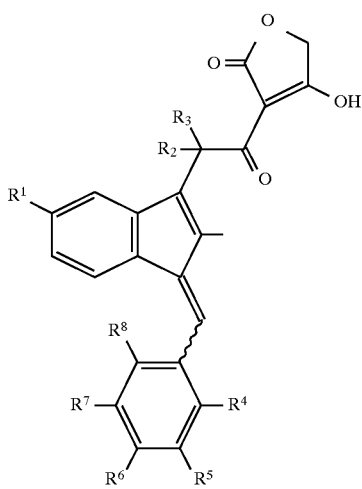

wherein:
R$^1$ is hydrogen, halogen, alkyl of 1–6 carbon atoms, alkoxy of 1–6 carbon atoms, fluoroalkoxy of 1–6 carbon atoms, trifluoromethyl, alkylthio of 1–3 carbon atoms, or SCF$_3$ R$^2$ and R$^3$ are each independently, hydrogen or alkyl of 1–6 carbon atoms, or R$^2$ and R$^3$ may be taken together to form a saturated cycloalkyl ring of 3–7 carbon atoms; and R$^4$, R$^5$, R$^6$, R$^7$ and R$^8$ are each independently, hydrogen, alkyl of 1–6 carbon atoms, alkoxy of 1–6 carbon atoms, alkylthio of 1–3 carbon atoms, alkylsulfinyl of 1–3 carbon atoms, alkylsulfonyl of 1–3 carbon atoms, halogen, fluoroalkoxy of 1–6 carbon atoms, CF$_3$, or SCF$_3$.

Preferred compounds of this invention are those of formula 2:

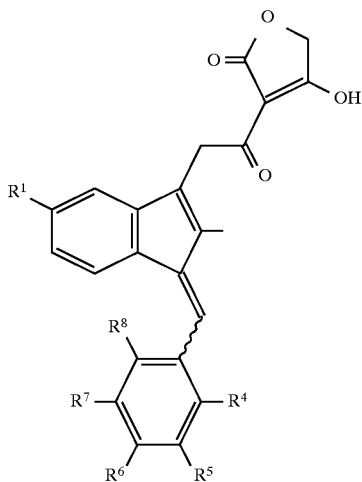

wherein
R$^1$ is lower alkoxy of 1–6 carbon atoms or halogen; and
R$^4$, R$^5$, R$^6$, R$^7$ and R$^8$ are each independently, hydrogen, halogen, thioalkyl of 1–3 carbon atoms, alkylsulfinyl of 1–3 carbon atoms, alkylsulfonyl of 1–3 carbon atoms, CF$_3$, or fluoroalkoxy of 1–6 carbon atoms.

More preferred compounds of this invention are those of formula 3:

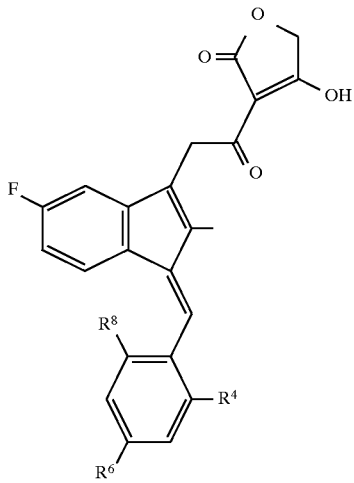

wherein
R$^4$, R$^6$ and R$^8$ are chlorine; or R$^4$ and R$^8$ are hydrogen and R$^6$ is thiomethyl.

Some of the compounds of this invention contain one or more asymmetric centers and may thus give rise to optical isomers and diastereomers. The present invention includes such optical isomers and diastereomers; as well as the racemic and resolved, enantiomerically pure R and S stereoisomers; as well as other mixtures of the R and S stereoisomers. Throughout this application wherever the absolute configuration at the asymmetric center is not indicated, it is intended to embrace both R and S enantiomers as well as mixtures of the two.

Certain compounds within the scope of the present invention exist in the form of E and Z stereoisomers and the individual isomers can be differentiated by the prefixes E and Z, as assigned by the accepted sequence rule procedures. Accordingly, the present invention embraces the E, Z and mixed isomer forms of those final product compounds exhibiting this form of stereoisomerism.

The term alkyl includes both straight chain as well as branched moieties. This includes the alkyl portions of substituents such as alkoxy, thioalkyl, alkylsulfinyl, alkylsulfonyl, fluoroalkoxy, and the like. The term halo includes fluorine, chlorine, bromine, and iodine. Fluoroalkoxy includes mono-, di-, tri-, and polyfluorinated alkoxy moieties such as —OCF$_3$, —OCH$_2$F, —OCHF$_2$, —OCH$_2$CF$_3$, and the like.

The tetronic acid derivatives of the present invention can be made by a variety of synthetic routes using conventional methods. According to one preparative scheme (Scheme I) an appropriately substituted indene 3-acetic acid of formula 4 is reacted with a tetronic acid to yield the desired final product of formula 1.

Scheme I

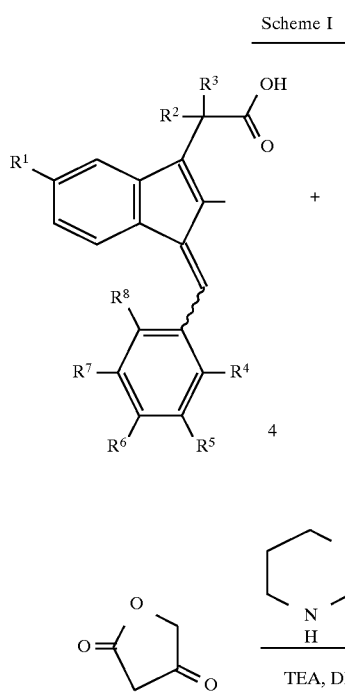

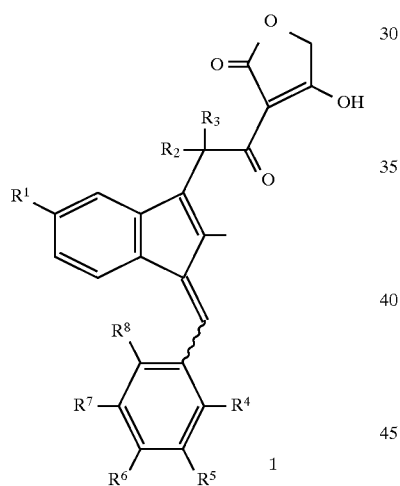

Scheme II

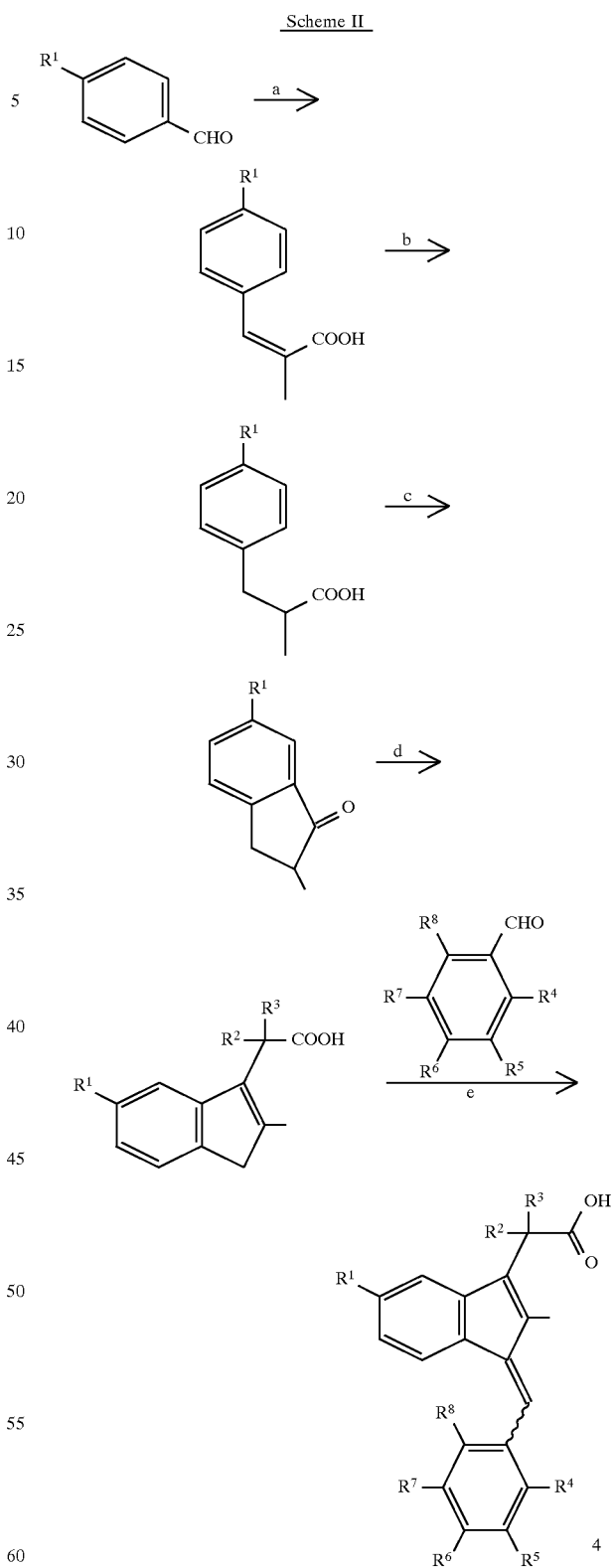

REAGENTS: (a) C$_2$H$_5$COOCOC$_2$H$_5$, C$_2$H$_5$COONa, heat; basify; acidify; (b) H$_2$, 5% Pd-C, EtOH; (c) PPA, heat; (d) NCC(R$^2$R$^3$)COOH, CH$_3$COONH$_4$, AcOH, toluene, heat; basify, acidify; (e) MeONa, MeOH; acidify The substituted indene 3-acetic acids starting materials of formula 4 can be prepared as described in U.S. Pat. No. 3,654,349. A preferred route is shown in Scheme II. Condensation of an appropriately substituted aromatic aldehyde with an acid anhydride and the sodium salt of the same acid provides the corresponding cinnamic acid. The intermediate cinnamic acid is hydrogenated in presence of a palladium catalyst to the corresponding hydrocinnamic acid. The intermediate hydrocinnamic acid is cyclized in hot polyphosphoric acid and the resulting indanone is condensed with a cyano acetic acid to provide the substituted indene 3-acetic acid. The intermediate indene 3-acetic acid is then condensed with an appropriately substituted aromatic aldehyde in the presence of an alkoxide to produce the intermediate indenyl acetic acid of formula 4.

The compounds of the present invention inhibit the COX-2 enzyme (Table 1) believed to be responsible for the production of high levels of prostaglandins in inflammation and certain types of cancer, such as colorectal cancer. It has been shown that preferential inhibition of the COX-2 enzyme relative to COX-1 inhibition leads to an anti inflammatory effect with substantially reduced G.I. toxicity (Chan et al, *J. Pharmacol. Exp. Ther.* 274, 1531–1537 (1995); Masferrer et al. *Proc. Natl. Acad. Sci. USA,* 91, 3228–3232 (1994); Seibert et al,, *Proc. Natl. Acad. Sci. USA,* 91, 12013–12017 (1994)). Futaki et al. (*Gen. Pharmac.* 24, 105–110, 1993) have reported that a selective COX-2 inhibitor N-(2-cyclohexyloxy-4-nitrophenyl)methanesulfonamide is an effective antiinflammatory and lacks gastric side effects. Therefore, the compounds of this invention by virtue of their inhibition of cyclooxygenase-2 and/or their specificity for cyclooxygenase-2 over cyclooxygenase-1, are for the treatment of inflammatory diseases such as rheumatoid arthritis and Alzheimer disease, and of certain types of cancer particularly in patients with peptic ulcers, gastric lesions and other gastric disorders because of their safer profile.

A representative compound of this invention was evaluated for inhibition of COX-2 and COX-1 enzymes as follows. Human COX-1 and COX-2 cDNAs were cloned from human monocytes, untreated and LPS-treated respectively, by RT-PCR using oligonucleotide primers based on published hCOX-1 and hCOX-2 sequences (Jones et al., *J. Biol. Chem.,* 268, 9049 (1993)). The cDNAs were then transfected into either Sf9 or CHO cells and subsequently converted into a microsomal preparation as described by Glaser et al (*Eur. J. Pharmacol.* 281, 107–111 (1995)). The microsomal human recombinant enzymes were diluted with buffer (100 mM Tris, pH 7.8 at 37° C.) containing 0.5 mM phenol (964 $\mu$l total volume). The enzyme preparations were preincubated with vehicle (DMSO) or compounds in DMSO (1% DMSO in final assay) for 30 min at 37° C. Excess hematin was added 1 min prior to initiation of reaction (1.25 $\mu$gM final hematin) with 30 $\mu$M arachidonic acid (sodium salt). Final assay volume was 1.0 ml (100 mM Tris (pH 7.8), 0.5 mM phenol, 1.25 $\mu$M hematin and 30 $\mu$M arachidonic acid at 37° C.).

The reaction was incubated for 35 sec (maximum level of $PGH_2$ accumulation as determined from time course studies), and terminated by addition of 50–60 mL of $SnCl_2$ (1 mg/ml) in 0.1N HCl. $PGH_2$ is quantitatively converted to $PGF_{2\alpha}$ by this reaction (50% efficiency of total conversion). The pH of each tube is adjusted to pH 3.0–3.5 with 1N-NaOH and extracted twice with 1.5 ml of ethyl acetate (75–90% efficiency per extraction). Combined ethyl acetate extracts were dried under $N_2$(g) and redissolved in EIA buffer (2.0 ml), and $PGF_{2\alpha}$ was quantified by EIA.

In all cases it has been found that similar results are obtained with either the recombinant human COX-1 or the purified ovine COX-1 enzymes, as reported in the literature (R. A. Copeland et al., *Proc. Natl. Acad. Sci. USA,* 91, 11202 (1994)). Accordingly, all the COX-1 data reported here are for the purified ovine COX-1 enzyme which was purchased from Cayman Chemicals (Ann Arbor, Mich.).

The results of the standard pharmacological test procedure described in the preceding paragraphs are shown below.

TABLE 1

Inhibition of rhCOX-2 and purified ovine COX-1 by indenyl tetronic acids

| Example | $R^4$ | $R^6$ | $R^8$ | % inh of rhCOX-2 ($IC_{50}$, $\mu$M) | % inh of purified ovine COX-1 ($IC_{50}$, $\mu$M) |
|---|---|---|---|---|---|
| 1 | H | $SCH_3$ | H | (0.027) | 100 (10 $\mu$M) |

The results in this standard pharmacological test procedures demonstrated high inhibition of the human COX-2 isozyme. Based on the results obtained in this test procedure, the compounds of this invention are useful for the treatment of arthritic disorders, Alzheimer disease and colorectal cancer. The compounds of this invention are also expected to have a high selectivity for the inhibition of the human COX-2 isozyme and would be expected to have a greater margin of G.I. safety in the treatment of arthritic disorders, Alzheimer disease, and colorectal cancer.

The compounds of this invention may be administered orally or parenterally, neat or in combination with conventional pharmaceutical carriers. Applicable solid carriers can include one or more substances which may also act as flavoring agents, lubricants, solubilizers, suspending agents, filers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets, preferably, contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount of therapeutically active compound that is administered and the dosage regimen for treating a specific arthritic disorder or colorectal cancer with the compound and/or compositions of this invention depends on a variety of factors, including the weight, age, sex, medical condition of the subject, the severity of the disease, the route and frequency of administration, and the specific compound employed, and thus may vary widely. The pharmaceutical compositions may contain active ingredient in the range of 0.1 to 2000 mg, preferably in the range of 0.5 to 500 mg and most preferably between 1 and 100 mg. Projected daily dosages of active compound are 0.01 to 100 mg/kg body weight. The daily dose of can be administered in one to four doses per day.

The following example illustrate the preparation of a representative compound of this invention.

EXAMPLE 1

(Z)-3-[[5-Fluoro-2-methyl-1-[[4-(methylthio)phenyl]methylene]-1H-inden-3-yl]acetyl]-4-hydroxy-2(5H)-furanone

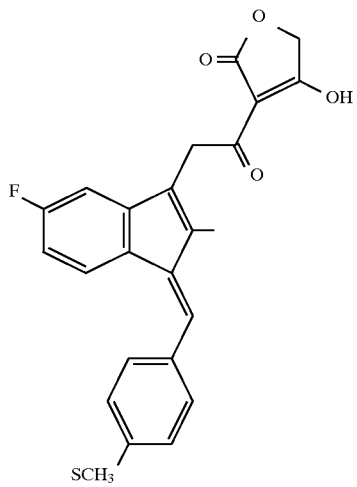

To a stirred suspension of tetronic acid (0.264 g, 2.64 mmol) in N,N-dimethylformamide (8.5 mL) kept at 0° C. was added under a nitrogen atmosphere triethylamine (0.396 mL) followed by 4-dimethylaminopyridine (0.138 mL, 0.974 mmol). The solution was stirred for 5 minutes and 5-fluoro-2-methyl-1-(4-methylthiobenzylidene)-3-acetic acid (1 g, 2.93 mmol; prepared as described in U.S. Pat. No. 3,654,349, which is hereby incorporated by reference) is added at 0° C., followed by 1-(3-dimethylaminopropyl)-3-ethyl carbodiimide hydrochloride (0.607 g, 3.16 mmol). The ice bath was removed and stirring continued overnight at room temperature. Additional triethylamine (0.39 mL) and 4-dimethylamino pyridine (0.138 g) were added and the mixture was stirred for two more days. The solvent was evaporated in vacuo and the residue diluted with water, and acidified to pH 4 with 1N HCl. The precipitated product was collected and the filtrate evaporated to dryness. The residue was flash chromatographed (on acid-treated silica Merck-60; eluant: toluene-EtOAc 7:3) to provide additional title compound. This material was combined with the precipitate obtained above and recrystallized from toluene (ethyl acetate)-ether to provide a bright yellow solid (45% yield), m.p. 178°–181° C. (dec).

Anal. Calcd. for $C_{24}H_{19}FO_4S$: C, 68.23; H, 4.53. Found: C, 68.13; H, 4.37. Mass spectrum (+FAB, m/z): 423 [M+H]$^+$, 445 [M+Na]$^+$ IR (KBr): 2920, 1760, 1735, 1650, 1600 cm$^{-1}$ NMR (400 MHz, DMSO-d$_6$): δ2.10 (s, 3H, CH$_3$), 2.52 (s, 3H, SCH$_3$), 4.06 (s, 2H, CH$_2$), 4.46 (s, 2H, CH$_2$), 4.2–4.7 (broad signal, exchangeable), 6.68 (m, 1H), 6.92 (m, 1H), 7.23 (s, 1H), 7.30 (m, 1H), 7.35 and 7.49 (m, 4H).

What is claimed is:

1. A compound of formula I having the structure

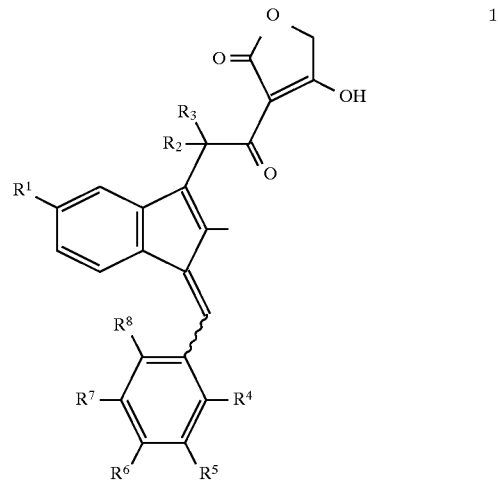

wherein:

$R^1$ is hydrogen, halogen, alkyl of 1–6 carbon atoms, alkoxy of 1–6 carbon atoms, fluoroalkoxy of 1–6 carbon atoms, trifluoromethyl, alkylthio of 1–3 carbon atoms, or $SCF_3$ $R^2$ and $R^3$ are each independently, hydrogen or alkyl of 1–6 carbon atoms, or $R^2$ and $R^3$ may be taken together to form a saturated cycloalkyl ring of 3–7 carbon atoms; and $R^4$, $R^5$, $R^6$, $R^7$ and $R^8$ are each independently, hydrogen, alkyl of 1–6 carbon atoms, alkoxy of 1–6 carbon atoms, alkylthio of 1–3 carbon atoms, alkylsulfinyl of 1–3 carbon atoms, alkylsulfonyl of 1–3 carbon atoms, halogen, fluoroalkoxy of 1–6 carbon atoms, $CF_3$, or $SCF_3$.

2. The compound according to claim 1 of formula 2 having the structure

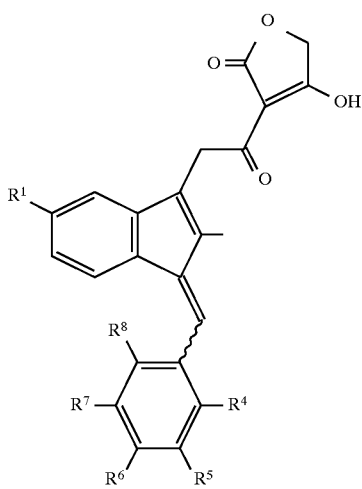

wherein

R¹ is lower alkoxy of 1–6 carbon atoms or halogen; and

R⁴, R⁵, R⁶, R⁷ and R⁸ are each independently, hydrogen, halogen, thioalkyl of 1–3 carbon atoms, alkylsulfinyl of 1–3 carbon atoms, alkylsulfonyl of 1–3 carbon atoms, CF₃, or fluoroalkoxy of 1–6 carbon atoms.

3. The compound according to claim 2 of formula 3 having the structure

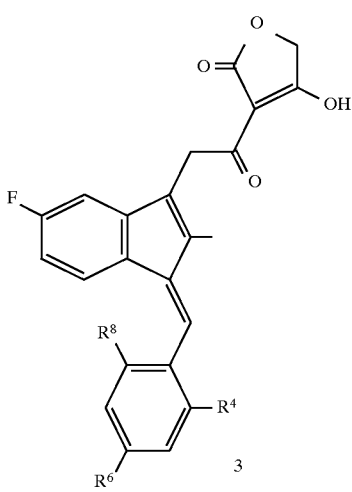

wherein

R⁴, R⁶ and R⁸ are chlorine; or R⁴ and R⁸ are hydrogen and R⁶ is thiomethyl.

4. The compound according to claim 1, which is (Z)-3-[[5-fluoro-2-methyl-1-[[4-(methylthio)phenyl]methylene]-1H-inden-3-yl]acetyl]-4-hydroxy-2(5H)-furanone.

5. A pharmaceutical composition which comprises a compound of formula 1 having the structure

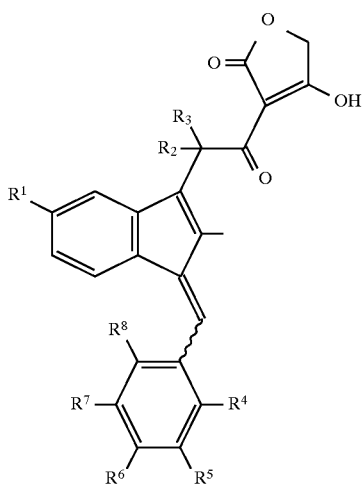

wherein:

R¹ is hydrogen, halogen, alkyl of 1–6 carbon atoms, alkoxy of 1–6 carbon atoms, fluoroalkoxy of 1–6 carbon atoms, trifluoromethyl, alkylthio of 1–3 carbon atoms, or SCF₃

R² and R³ are each independently, hydrogen or alkyl of 1–6 carbon atoms, or R² and R³ may be taken together to form a saturated cycloalkyl ring of 3–7 carbon atoms; and R⁴, R⁵, R⁶, R⁷ and R⁸ are each independently, hydrogen, alkyl of 1–6 carbon atoms, alkoxy of 1–6 carbon atoms, alkylthio of 1–3 carbon atoms, alkylsulfinyl of 1–3 carbon atoms, alkylsulfonyl of 1–3 carbon atoms, halogen, fluoroalkoxy of 1–6 carbon atoms, CF₃, or SCF₃ and a pharmaceutical carrier.

* * * * *